(12) United States Patent
Surulichamy et al.

(10) Patent No.: US 8,148,520 B2
(45) Date of Patent: Apr. 3, 2012

(54) PROCESS FOR THE PREPARATION OF BETA-LACTAM ANTIBIOTIC MEROPENEM TRIHYDRATE

(75) Inventors: Senthilkumar Surulichamy, Chennai (IN); Selvakumar Sekar, Chennai (IN); Pramod Narayan Deshpande, Chennai (IN); Panchapakesan Ganpathy, Chennai (IN); Rajendra Janardan Sarangdhar, Chennai (IN); Syril Sudhan Henry, Chennai (IN); Sanjay Nivruti Karale, Aurangabad (IN); Arvind Atmaram Jangale, Aurangabad (IN); Ram Dattatray Kaldate, Aurangabad (IN)

(73) Assignee: Orchid Chemicals and Pharmaceuticals Limited, Chennai (IN)

( * ) Notice: Subject to any disclaimer, the term of this patent is extended or adjusted under 35 U.S.C. 154(b) by 643 days.

(21) Appl. No.: 11/991,624

(22) PCT Filed: Sep. 15, 2006

(86) PCT No.: PCT/IB2006/002548
§ 371 (c)(1),
(2), (4) Date: Apr. 30, 2009

(87) PCT Pub. No.: WO2007/031858
PCT Pub. Date: Mar. 22, 2007

(65) Prior Publication Data
US 2009/0264643 A1    Oct. 22, 2009

(30) Foreign Application Priority Data
Sep. 15, 2005 (IN) ............................ 1301/CHE/2005
Aug. 22, 2006 (IN) ............................ 1486/CHE/2006

(51) Int. Cl.
*C07D 477/20* (2006.01)
(52) U.S. Cl. ...................................................... 540/350
(58) Field of Classification Search .................. 540/350
See application file for complete search history.

(56) References Cited

U.S. PATENT DOCUMENTS

| 4,888,344 A | 12/1989 | Sunagawa et al. |
| 4,943,569 A | 7/1990 | Sunagawa |
| 6,548,492 B1 | 4/2003 | Al-Dehneh et al. |
| 2009/0299057 A1* | 12/2009 | Khemka et al. ............... 540/350 |

FOREIGN PATENT DOCUMENTS

| EP | 0 256 377 A1 | 2/1988 |
| IN | 2007MU02068 | * 2/2008 |
| WO | WO 99/14218 | 3/1999 |
| WO | WO 2005/118586 | 12/2005 |
| WO | WO 2006/035300 A2 | 4/2006 |

OTHER PUBLICATIONS

Prashad, Tetrahedron Letters (1998), 39(39), 7035-7038.*
Nishioka, Journal of Labelled Compounds and Radiopharmaceuticals (1991 ), 29(9), 1051-60.*
Translation of Zhao, Chinese Journal of Medicinal Chemistry, vol. 15, No. 2, Apr. 2005, Sum 64, pp. 97-99.*
Zhao et al., "Synthesis of meropenem trihydrate," Chinese Journal of Medicinal Chemistry, vol. 15, No. 2, p. 97-99, 2005.

* cited by examiner

*Primary Examiner* — Mark Berch
(74) *Attorney, Agent, or Firm* — Oliff & Berridge, PLC

(57) ABSTRACT

A process for preparing purified Meropenem trihydrate that involves the dissolution of Meropenem in water in presence of base, adjusting the pH to 4.0-7.0, and adding solvent to yield Meropenem trihydrate.

4 Claims, 1 Drawing Sheet

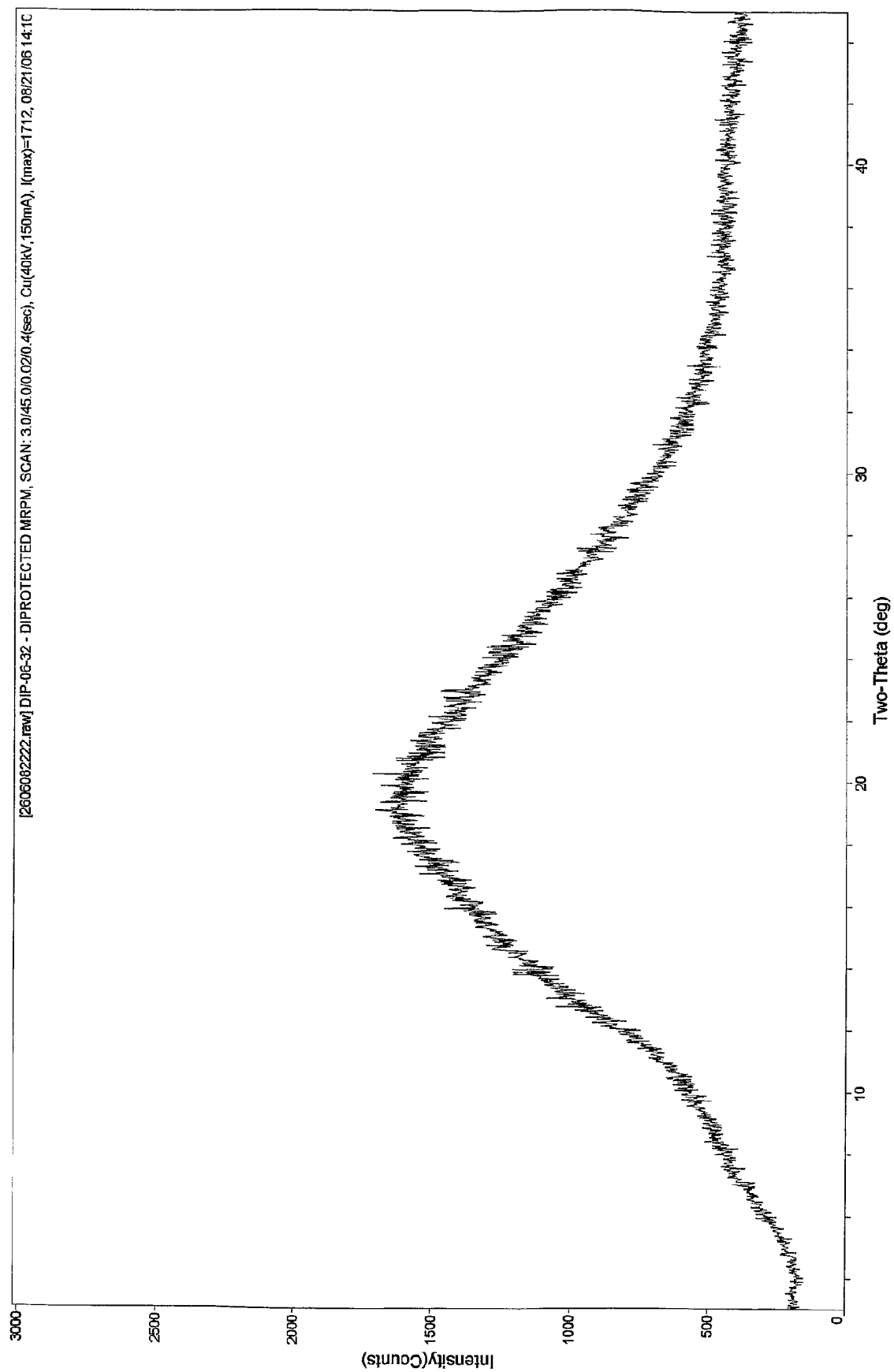

PROCESS FOR THE PREPARATION OF BETA-LACTAM ANTIBIOTIC MEROPENEM TRIHYDRATE

FIELD OF THE INVENTION

The present invention provides an improved process for the preparation of the compound of formula (I) or its hydrate in a pure form.

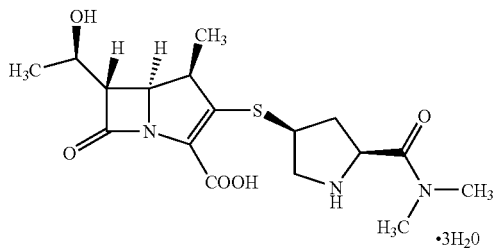

(I)

The present invention further provides an improved process for the preparation of compound of formula (V) in amorphous form, which is an important intermediate in the preparation of Meropenem of formula (I)

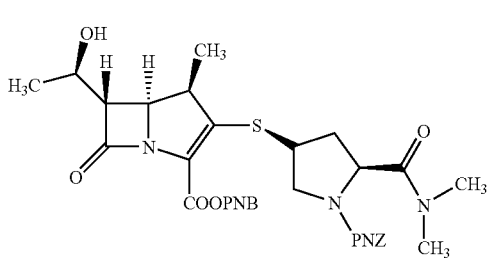

(V)

wherein PNB represents p-nitrobenzyl group and PNZ represents (p-nitrobenzyloxycarbonyl group.

BACKGROUND OF THE INVENTION

Meropenem is a broad spectrum, beta-lactamase-resistant, carbapenem antibiotic for parenteral administration. The compound of the formula (I) is generically known as meropenem and is used as antibiotic agent in the treatment of pneumonia, urinary tract infections, intra-abdominal, gynaecological, skin, and soft tissue infections, meningitis, septicemia and febrile neutropenia. In USA it is sold under the trade name of MERREM® I.V. (meropenem for injection). MERREM is a sterile, pyrogen-free, synthetic, broad spectrum, carbapenem antibiotic for intravenous administration, and chemically known as (4R,5S,6S)-3-[[(3S,5S)-5-(dimethylcarbamoyl)-3-pyrrolidinyl]thio]-6-[(1R)-1-hydroxyethyl]-4-methyl-7-oxo-1-azabicyclo[3.2.0]hept-2-ene-2-carboxylic acid trihydrate. In view of the importance of the compound of the formula (I), several synthetic procedures to prepare the compound have been reported.

U.S. Pat. No. 4,888,344 provides crystalline Meropenem trihydrate along with non-toxic carbonate composition. According to this patent, Meropenem was obtained by deprotecting the protecting groups of the penultimate compound by hydrogenation as per the following scheme.

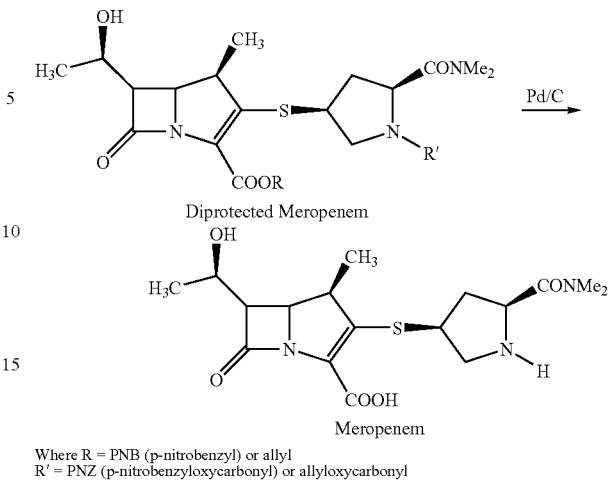

Where R = PNB (p-nitrobenzyl) or allyl
R' = PNZ (p-nitrobenzyloxycarbonyl) or allyloxycarbonyl U.S. Pat. No. 4,943,569 claims Meropenem and process for its preparation. This patent utilizes buffer like morpholinoalkyl sulfonic acid (MOPS) or its salt during deprotection stage. The description also discloses that the penultimate intermediate (diprotected Meropenem) of Meropenem can be isolated by organochemical means.

According to the above said patents, Meropenem trihydrate was obtained by subjecting the aqueous reaction mass obtained after the deprotection of protecting group, to reverse osmosis (if required), followed by adding water-miscible organic solvent such as ethanol, iso-propanol, acetone, tetrahydrofuran (THF), dioxane, acetonitrile, etc.

IN 198820 provide a method for the preparation of Meropenem wherein biphasic solvent system such as Water-THF-Ethyl acetate was utilized for deprotection (where R' is allyloxycarbonyl). After deprotection of the protecting groups, the aqueous layer was subjected to crystallization of meropenem trihydrate by the addition of THF.

WO2006/035300 A2 describes a process for preparing Meropenem. This patent publication describes the use of biphasic solvent system for the deprotection step resulting in Meropenem, which is similar to the teachings given in U.S. Pat. No. 4,943,569, where ethyl acetate was added after the hydrogenation to remove organic impurity, and obvious over our Indian patent, 198820. Even though U.S. Pat. No. 4,943,569 teaches the isolation of penultimate, which is not necessary as mentioned, "After completion of the reaction, the reaction product (i.e formula (V)) can be isolated by usual organochemical means"; WO2006/035300A2 publication claims a process for preparing Meropenem trihydrate in which the penultimate compound of formula (V) was not isolated. Similarly, U.S. Pat. No. 4,888,344, which teaches "when the catalytic hydrogenation is carried out in a water-containing organic solvent, the filtrate obtained by filtration of the reaction mixture for removal of the catalyst may be subjected to distillation for evaporation of the organic solvent. In such case, Compound A (Meropenem trihydrate) can be crystallized out directly from the resultant aqueous concentrate. Thus, crystalline Compound A is obtainable without separation and isolation of non-crystalline Compound A, for instance, by column chromatography or lyophilization", claims a direct process for preparing Meropenem trihydrate in which the crystallization is done directly after deprotection.

WO2005/118586 A1 claims crystalline penultimate compound of formula (V) and a process for preparing this intermediate. According to this publication this intermediate is crystallized out either from concentrating the mother liquor in alkyl alkanoate such as ethyl acetate or by the addition of anti-solvent such as cyclohexane or heptane to the mother liquor in ethyl acetate. Since this patent describes the use of multiple solvent systems, the processes are not commercially viable from industrial point of view owing to multiple solvent recoveries, adding further the cost of production.

As per U.S. Pat. No. 4,888,344 in example 1, Meropenem is dissolved in water, where upon small amount of meropenem crystals formed and further addition of acetone yielded meropenem trihydrate. Since the sterile preparation requires complete dissolution for sterile filtration, this technique is not found attractive.

With our continued research for developing a process for the preparation of compound of formula (I) as sterile product, we have come up with a process, which is not only commercially viable, but also involves simple techniques such as crystallizations, isolation of the penultimate of formula (V) avoiding multiple solvents. None of the prior art suggests or teaches the techniques of the present invention.

OBJECTIVES OF THE INVENTION

The main objective of the present invention is to provide a simple and commercially viable process for the preparation of compound of the formula (I) as sterile product in pure form.

Another objective of the present invention is to provide a simple and commercially viable process for the preparation of compound of the formula (I), which avoids chromatographic techniques.

Yet another objective of the present invention is to provide a simple and commercially viable process for the preparation of compound of the formula (V), which avoids multiple solvent systems.

SUMMARY OF THE INVENTION

Accordingly, the present invention provides a process for the preparation of Meropenem trihydrate of formula (I), which comprises the steps of:

(a) dissolving Meropenem or its trihydrate in water in the presence or absence of water-miscible organic solvent and in the presence of base, (b) optionally filtering through micron filter, (c) adjusting pH to 4.0 to 7.0 using acid, and (d) optionally adding solvent to precipitate the Meropenem trihydrate of formula (I),

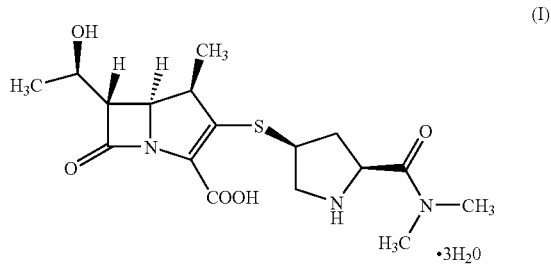

The present invention further provides an improved process for preparation of compound of formula (V), which comprises the steps of:

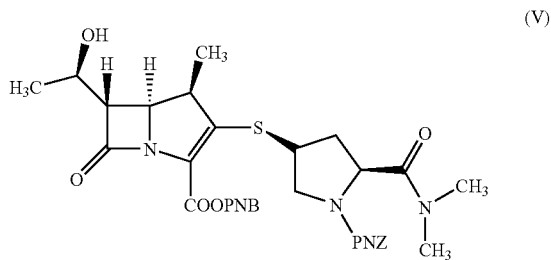

(1) reacting the activated compound of formula (III) with mercaptan of formula (IV) in the presence or absence of base in a water-miscible organic solvent, (2) precipitating the compound of formula (V) obtained in step (1) by mixing the reaction mass from step (1) with water in the presence or absence of buffer, (3) optionally adjusting the pH to 3.0 to 5.0, (4) filtering the compound of formula (V).

In another embodiment of the present invention there is provided an improved process for preparation of compound of the formula (I), the said process comprising the steps of:

(i) activating the compound of formula (II) using an activating reagent in the presence or absence of base and solvent to produce compound of formula (III), (ii) reacting the activated compound of formula (III) with mercaptan of formula (IV) in the presence or absence of base and solvent to yield compound of formula (V), (iii) deprotecting the compound of formula (V) by catalytic hydrogenation to yield compound of formula (I), and (iv) optionally converting the compound of formula (I) into sterile compound of formula (I).

The process is shown in Scheme-I as given below:

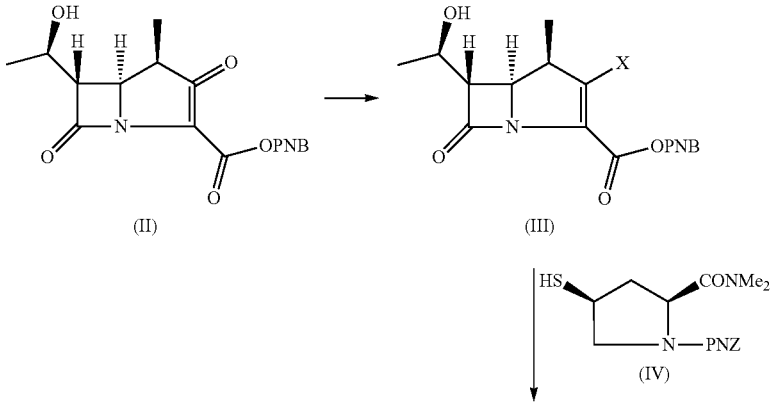

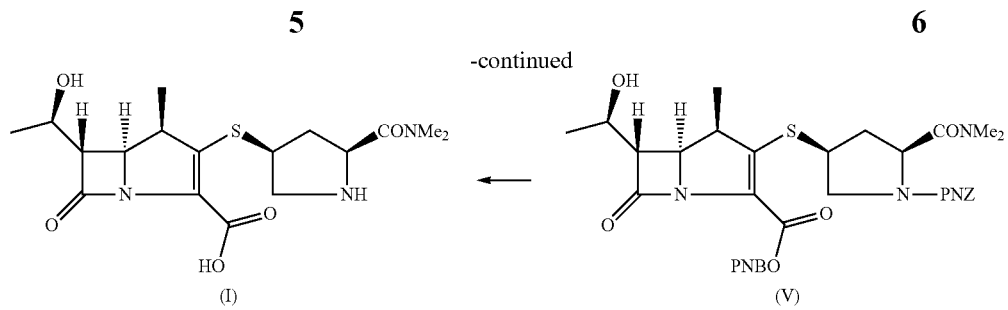

-continued

DRAWINGS OF THE INVENTION

FIG. 1: PXRD of amorphous form of diprotected meropenem intermediate of compound of formula (V).

DETAILED DESCRIPTION OF THE INVENTION

In an embodiment of the present invention, the base used in step (a) is selected from ammonia, sodium hydroxide, sodium carbonate, potassium carbonate, diethylamine, diisopropylamine, triethylamine, diisopropylethylamine, sodium bicarbonate, potassium bicarbonate, sodium acetate, sodium-2-ethyl hexanoate, sodium lactate and the like, preferably ammonia and water-miscible organic solvents used in step (a) is selected from acetone, methanol, ethanol, isopropanol, 1-propanol, THF, acetonitrile or mixtures thereof.

In another embodiment of the present invention, the acid used in step (c) is elected from HCl, formic acid, oxalic acid, acetic acid, methane sulfonic acid, sulfuric acid, phosphoric acid, trifluoroacetic acid and the like, preferably formic acid.

In yet another embodiment of the present invention, the solvent used in step (d) is selected from THF, acetone, methyl ethyl ketone, methanol, isopropanol, 1-propanol, ethanol and the like or mixtures thereof, preferably THF.

In one more embodiment of the present invention, the starting material, non-sterile Meropenem or its trihydrate is prepared by utilizing the process given in our Indian patent, 198820 or by utilizing the process according to our present invention or by any conventional methods.

In still another embodiment, the present invention can be used for the purification of Meropenem trihydrate to achieve highly pure Meropenem trihydrate by performing steps (a), (c) and (d).

In another embodiment of the present invention, the base used in step (1) is an organic amine selected from diisopropylamine, diisopropylethylamine, triethylamine, pyridine, N,N-dimethylaminopyridine, N,N-diethylaminopyridine, tetramethylguanidine (TMG) and the like or mixture thereof.

In still another embodiment of the present invention, water-miscible organic solvent used in step (1) is selected from tetrahydrofuran, N,N-dimethylformamide, N,N-dimethylacetamide, N-methylpyrrolidinone, N-ethylpyrrolidinone, N-methylpiperidinone, acetonitrile, propionitrile, acetone, ethanol, methanol, isopropyl alcohol, 1-propanol, methyl ethyl ketone, DMSO and other such organic solvents known in the art or mixture thereof.

In yet another embodiment of the present invention, the diprotected compound of the formula (V) is precipitated from the reaction medium by mixing the reaction mass into water or buffer solution or vice versa followed by filtering the solid obtained thereof. Optionally the pH of the reaction mass in step (3) was adjusted to the pH in the range of 3.0 to 5.0 and more specifically 3.6 to 4.2 using acid such as sulphuric acid, hydrochloric acid and the like. The compound thus isolated is in amorphous form. Alternatively the compound of formula (V) is used further in situ for the preparation of compound of formula (I) thereby avoids the need of isolation. The filtered compound of formula (V) is taken to further steps either as a wet or dry material.

In another embodiment of the present invention, the activating group represented by X in formula (III) is selected from diphenyl phosphate, 2,4-dichlorodiphenyl phosphate, diethyl thiophosphate, tosylate, mesylate and the like preferably diphenyl phosphate and the activating reagent used in step (i) is selected from diphenyl chlorophosphate, 2,4-dichlorodiphenylchloro phosphate, diethyl chlorothiophosphate, p-toluenesulphonyl chloride, methanesulphonyl chloride.

In another embodiment of the present invention, the base used in step (i) or (ii) is selected from diisopropylamine, ethyldiisopropylamine, triethylamine, pyridine, N,N-dimethylaminopyridine, N,N-diethylaminopyridine and the like or the mixtures thereof. If a mixture of base was employed then one of the bases can be used in catalytic amount over the other.

In still another embodiment of the present invention, the solvent used in step (i) or (ii) is selected from diethyl ether, tetrahydrofuran, toluene, xylene, dichloromethane, 1,2-dichloroethane, N,N-dimethylformamide, dimethylacetamide, N-methylpyrrolidinone, N-ethylpyrrolidinone, N-methylpiperidinone, acetonitrile, propionitrile, and other such organic solvents known in the art or mixtures thereof.

Accordingly, this invention also provides a common process for isolation of compound of formula (III) or (V) which comprises quenching the reaction mass obtained into a buffer solution selected from dipotassium hydrogen orthophosphate, potassium dihydrogen orthophosphate, and the like followed by extracting the compound in an organic solvent like ethyl acetate, MDC (dichloromethane), THF and the compound of formula (III) or (V) was precipitated as white to off-white solid or paste in a crystalline or amorphous forms or as a foamy solid using hexane or IPE (diisopropylether) or methyl tert-butyl ether.

In one more embodiment of the present invention, the solvent used in the deprotection stage in step (iii) is selected from THF, dioxane, ethyl acetate, isopropyl alcohol, dichloromethane, DMF, or mixtures thereof and water, and catalyst employed for reduction is selected from platinum oxide, Pd/C, Pt/C and the like.

The starting material used in the present invention is prepared by utilizing the process available in the literature, or by utilizing the process given in Heterocycles 1984, 21, 29 as per the scheme depicted below:

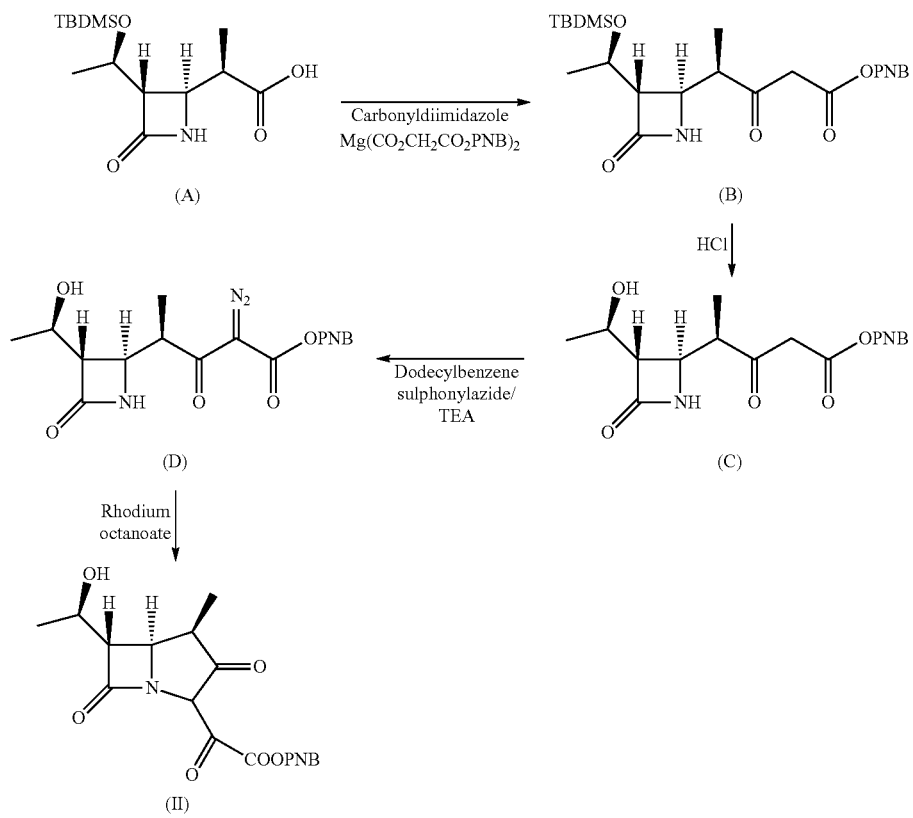

Accordingly the starting material of the present invention is prepared as follows: The compound of formula (C), (3S, 4R)-3-[(1R)-1-hydroxyethyl]-4-[(1R)-1-methyl-3-p-nitrobenzyloxycarbonyl-2-oxopropyl]-2-azetidine-2-one (which is prepared by treating azetidinone carboxylic acid with Mg salt of malonic acid mono p-nitrobenzyl ester in the presence of carbonyldiimidazole at 25-30° C., followed by quenching the reaction mass to water containing ammonium chloride, and extracting the product using ethyl acetate and treating the ethyl acetate layer with hydrochloric acid solution followed by quenching ethyl acetate layer to ether to afford compound of formula (C)) was converted into compound of formula (D) using 4-dodecylbenzenesulphonylazide in the presence of solvent like acetonitrile, hexane and an organic base like TEA, the compound of formula (D) was isolated from the reaction mass by treating the reaction mass with hexane and buffer solution followed by extracting into organic solvent like ethyl acetate or MDC. The conversion of compound of formula (D) into compound of formula (II) is carried out by using rhodium salt preferably rhodium octanoate and optionally in the presence of Lewis acid such as zinc halide preferably zinc iodide or zinc bromide.

The foregoing technique has been found to be attractive from commercial, technological and ecological perspective. The technique given in the present invention can also be extended to the preparation of other penems like Panipenem, doripenm, Ertapenem and the like by simply replacing the corresponding mercaptan. The penems thus obtained according to present invention can also be administered in the conventional methods. The conventional pharmaceutical composition may also contain one or more of the following: chelating agent such as EDTA; or buffering agent like citric acid; or amino acids like arginine; or sodium carbonate, potassium carbonate, sodium bicarbonate, potassium bicarbonate and the like. It has been found that in the presence of EDTA or citric acid or both increase the stability and solubility of the conventional pharmaceutical composition of Meropenem, Panipenem, Doripenm, Ertapenem, Imipenem, Aztreonam, Faropenem, Biapenem or its salts, hydrates and solvates.

The present invention is further illustrated by the following examples that are not intended as a limitation of the scope of the invention.

EXAMPLE 1

Preparation of Sterile Meropenem Trihydrate

Into a cold suspension of non-sterile Meropenem trihydrate (100 g) in water (750 mL) ammonia solution was added drop-wise till clear solution was obtained. The clear solution was subjected to carbon treatment followed by micron filtration (series of micron filtrations with numbers 5.0, 1.2 and 0.2µ) in sterile area and pH of filtrate was adjusted to approximately 5 to 6 using aqueous formic acid. THF was added to the resultant mass. The solid obtained was filtered, washed with aqueous tetrahydrofuran, and dried to yield the title compound in pure form. (Purity: 99.00-99.88%; water content: 11.4 to 13.4%).

EXAMPLE 2

Preparation of Meropenem Trihydrate

Into a suspension of non-sterile Meropenem trihydrate (100 g) in water (750 mL) ammonia solution was added drop-wise till clear solution was obtained. To the clear solution, EDTA, sodium hydrosulfite were added then subjected to carbon treatment followed and pH of filtrate was adjusted to approximately 5 to 6 using aqueous formic acid. THF was added to the resultant mass. The solid obtained was filtered, washed with aqueous tetrahydrofuran, and dried to yield the title compound in pure form. (Purity: 99.40-99.81%; water content: 11.54 to 13.40%).

Advantages:

The procedure given in U.S. Pat. No. 4,888,344 is not suitable for sterile preparation as Meropenem does not remain in solution long enough to perform sterile filtration in sterile area. As meropenem trihydrate is administered as an injectable solution, the present invention provides a solution to prepare sterile Meropenem trihydrate. Also the present invention provides a purification process to obtain highly pure compound.

EXAMPLE 3

Preparation of Meropenem Trihydrate

Step (i)

Preparation of (4R,5R,6S)-3-[(diphenoxyphosphoryloxy]-6-[(R)-1-hydroxyethyl]-4-methyl-7-oxo-1-azabicyclo[3.2.0]-hept-2-ene-2-carboxylicacid-(4-nitrophenyl)methyl ester (III)

To the solution of (4R,5R,6S)-4-methyl-6-[(R)-1-hydroxyethyl]-1-azabicyclo[3.2.0]hept-3,7-dione-2-carboxylic acid (4-nitrophenyl)methyl ester of formula (II) (100 g) in acetonitrile (500 mL) at −10° C. were added N-ethyldiisopropylamine (54 g) and diphenylchlorophosphate (82 g) and stirred at −10° C. After completion of the reaction, the resultant mass was quenched into the mixture containing dipotassium hydrogen orthophosphate buffer and ethyl acetate and stirred for 15 min. The ethyl acetate layer was separated and washed with phosphate buffer. Diisopropyl ether was added to the ethyl acetate layer and stirred for an hour. The precipitated solid was filtered and dried to yield the title compound (75 g, purity 98%).

Step (ii)

Preparation of (4R,5S,6S,8R,2'S,4'S)-p-Nitrobenzyl-3-[4-(1-p-nitrobenzyloxycarbonyl-2-dimethylaminocarbonyl)pyrrolidinylthio]-4-methyl-6-(1-hydroxyethyl)-1-azabicyclo[3.2.0]-hept-2-en-7-one-2-carboxylate (V)

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester in acetonitrile (1660 mL) were added (2S,4S)-1-p-nitrobenzyloxycarbonyl-2-dimethylaminocarbonylamino-4-mercaptopyrrolidine (66 g) and N-ethyldiisopropylamine (36 mL) at −15° C. and stirred under nitrogen atmosphere. After completion of the reaction, the resultant mass was quenched into ethyl acetate containing dipotassium hydrogen orthophosphate and stirred for 15 min. The ethyl acetate layer was distilled out completely under vacuum. The residue was dissolved in ethyl acetate and stirred. To the precipitated mass was added diisopropylether and stirred for an hour. The solid was filtered and dried to yield the title compound (110 g, Purity: 98%).

Step (iii)

(a). Preparation of (4R,5S,6S,8R,2'S,4'S)-3-[4-(2-Dimethylaminocarbonyl)pyrrolidinylthio]-4-methyl-6-(1-hydroxyethyl)-1-azabicyclo[3.2.0]hept-2-en-7-one-2-carboxylic acid (Meropenem trihydrate)

(4R,5S,6S,8R,2'S,4'S)-p-Nitrobenzyl-3-[4-(1-p-nitrobenzyloxycarbonyl-2-dimethylaminocarbonyl)pyrrolidinylthio]-4-methyl-6-(1-hydroxyethyl)-1-azabicyclo[3.2.0]hept-2-en-7-one-2-carboxylate (100 g) obtained from Step (ii) was dissolved in ethyl acetate, tetrahydrofuran (1000 mL), water (1000 mL) and 10% palladium-carbon (200 g) were added thereto, and introduced hydrogen therein at room temperature under a hydrogen pressure by maintaining a pH in the range of about 3.5. After completion of the reaction, the catalyst was removed by filtration, and the filtrate was washed with water; the aqueous layers were separated, and washed with ethyl acetate. The aqueous layer was treated with carbon, and the filtrate was poured into excess THF. The solid obtained was filtered and dried to yield the title compound (38 g; Purity 98-99.5%).

(b). Preparation of Meropenem Trihydrate (5R,6S,8R,2'S,4'S)-p-Nitrobenzyl-3-[4-(1-p-nitrobenzyloxycarbonyl-2-dimethylamino carbonyl)pyrrolidinylthio]-6-(1-hydroxyethyl)-4-methyl-7-oxo-1-azabicyclo[3,2,0]hept-2-ene-2-carboxylate (50 g) was taken in THF (500 mL) then stirred to get clear solution and water (500 mL) was added thereafter. The reaction mass was subjected to hydrogenation with 10% palladium on carbon (50 g) for 2-3 h at 25-30° C. with 9-10 kg hydrogen pressure. After hydrogenation, ethyl acetate (500 mL) was added to the reaction mixture. The palladium-carbon was filtered off and the organic layer separated. The aqueous layer was extracted into ethyl acetate. Then the aqueous layer was charcoalised followed by degassing to remove traces of ethyl acetate. Carbon was filtered off and washed with water. To the aqueous layer, excess THF was added slowly at to precipitate Meropenem trihydrate. The product was filtered and washed with aqueous THF to afford the title compound (19 g) as off-white crystals with 98% purity.

EXAMPLE 4

(a). Preparation of Meropenem Trihydrate

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester (50 g) in acetonitrile (500 mL) was added (2S,4S)-1-p-nitrobenzyloxycarbonyl-2-dimethylaminocarbonylamino-4-mercaptopyrrolidine (33 g) and N-diisopropylethylamine (14 g) at −15° C. and stirred. After the reaction was over, the reaction mixture was quenched in phosphate buffer solution. The product was extracted into ethyl acetate and washed with water. The organic layer was subjected to carbon treatment, filtered off and evaporated under vacuum to get thick paste (foam nature). To the thick paste was added ethyl acetate and THF to get clear solution followed by water. The reaction mass was subjected to hydrogenation with 10% palladium on carbon for 2-3 h at 25-30° C. with 9-10 kg pressure of hydrogen. The palladium carbon was filtered off and the organic layer separated. The aqueous layer was charcoalised followed by degassing to remove the ethyl acetate, filtered and the carbon bed washed with water. To the aqueous layer was added excess THF to precipitate the product. The product was filtered, washed with aqueous THF and dried to afford the title compound (22 g) as off-white crystals.

(b). Preparation of Meropenem Trihydrate

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester (50 g) in acetonitrile (500 mL) was added (2S,4S)-1-p-nitrobenzyloxycarbonyl-2-dimethylaminocarbonylamino-4-mercaptopyrrolidine (33 g) and N-ethyldiisopropylamine (14 g) at −15° C. and stirred. After the reaction was over, the reaction mixture was quenched in phosphate buffer solution. The product was extracted into ethyl acetate and washed with water. The organic layer was subjected to carbon treatment, filtered off and evaporated by vacuum to get the thick paste. To the thick paste was added THF then stirred to get clear solution and water was added thereafter. The reaction mass was subjected to hydrogenation with 10% palladium on carbon (50 g) with 9-10 kg hydrogen pressure. After the hydrogenation, ethyl acetate (500 mL) was added to reaction mixture. The palladium carbon was filtered off and the organic layer separated. The aqueous layer was extracted with ethyl acetate then separated. Then aqueous layer was charcoalised followed by degassing to remove ethyl acetate. Carbon was filtered off and washed with water. To the aqueous layer, excess THF was added to precipitate Meropenem trihydrate. The product was filtered and washed with aqueous THF to afford the title compound (22 g) as off-white crystals with 98% purity.

(c). Preparation of Meropenem Trihydrate

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester (50 g) in acetonitrile (500 mL) were added (2S,4S)-1-p-nitrobenzyloxycarbonyl-2-dimethylaminocarbonylamino-4-mercaptopyrrolidine (33 g) and N-ethyldiisopropylamine (14 g) at −15° C. and stirred. After the reaction was over, the reaction mixture was quenched in phosphate buffer solution. The product was extracted into ethyl acetate and washed with water. The organic layer was subjected to carbon treatment, filtered off and evaporated under vacuum to give (4R,5S,6S,8R,2'S,4'S)-p-nitrobenzyl-3-[4-(1-p-nitrobenzyloxycarbonyl-2-dimethylaminocarbonyl)pyrrolidinylthio]-4-methyl-6-(1-hydroxyethyl)-1-azabicyclo[3.2.0]-hept-2-en-7-one-2-carboxylate (amorphous in nature). To this was added THF and stirred to get clear solution followed by water (900 mL). The reaction mass subjected to hydrogenation with 10% palladium on carbon (50 g) for 2-3 h at 25-30° C. with 9-10 kg pressure of hydrogen. After hydrogenation was added ethyl acetate (500 mL). Then palladium carbon was filtered off and the organic layer separated. The aqueous layer was extracted with ethyl acetate then separated. Then the aqueous layer was charcoalised followed by degassing to remove ethyl acetate, filtered and washed with water. To the aqueous layer was added aqueous THF. The product was filtered, washed with aqueous THF and dried to afford the title compound (21.5 g) as off white crystals with 98% purity.

(d). Preparation of Meropenem Trihydrate

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester (50 g) in acetonitrile (500 mL) was added (2S,4S)-1-p-nitrobenzyloxycarbonyl-2-dimethylaminocarbonylamino-4-mercaptopyrrolidine (32 g) and N-ethyldiisopropylamine (14 g) at −15° C. and stirred. After the reaction was over, the reaction mixture was quenched in phosphate buffer solution. The product was extracted with ethyl acetate and washed with water. The organic layer was subjected to carbon treatment, filtered off and evaporated under vacuum to get thick paste. To the thick paste was added ethyl acetate and THF to get clear solution followed by water. This solution was washed with brine solution and the layers separated. To the reaction mass, water was added and subjected to hydrogenation with 10% palladium on carbon. The palladium carbon was filtered off and the organic layer separated. The aqueous layer was subjected to carbon treatment, filtered and washed with water. To the aqueous layer was added excess acetone to precipitate the product. The product was filtered, washed with aqueous acetone and dried to afford the title compound (22 g) as off white crystals.

EXAMPLE 5

(a). Preparation of Meropenem Trihydrate

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester (50 g) and (2S,4S)-1-p-nitrobenzyloxycarbonyl-2-dimethylaminocarbonylamino-4-mercaptopyrrolidine (33 g) in N,N-dimethylformamide (250 mL) was added slowly diisopropylethylamine (14 g) at −40 to −10° C. and stirred for 2-3 h. The reaction mass was then added slowly to the phosphate buffer to isolate the solid product. The pH was then adjusted to 3.8 to 4.0 using sulphuric acid at 5-10° C. then stirred for an hour. The isolated (4R,5S,6S,8R,2'S,4'S)-p-nitrobenzyl-3-[4-(1-p-nitrobenzyloxycarbonyl-2-dimethylaminocarbonyl)pyrrolidinylthio]-4-methyl-6-(1-hydroxyethyl)-1-azabicyclo[3.2.0]hept-2-en-7-one-2-carboxylate (V) was filtered and washed with water.

The isolated wet product was dissolved in THF (550 mL), then water (400-450 mL) added and the pH adjusted to 3.8 to 4.5 using sulphuric acid solution. The reaction mass was subjected to hydrogenation with 10% palladium on carbon (55 g) at 25-30° C. with 9-10 kg pressure of hydrogen. The palladium-carbon was filtered off and the filtrate washed with ethyl acetate. The aqueous layer was charcoalised. To the aqueous filtrate was added slowly cold THF. The product was filtered and washed with aqueous THF to afford the title compound (22.0 g) as off white crystal.

(b). Preparation of Meropenem Trihydrate

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester (50 g) and (2S,4S)-1-p-nitrobenzyloxycarbonyl-2-dimethylaminocarbonylamino-4-mercaptopyrrolidine (33 g) in N,N-dimethylformamide (250 mL) was added slowly diisopropylethylamine (14 g) at −40 to −10° C. then stirred for 2-3 h. The reaction mass was then added slowly to the phosphate buffer to isolate the solid product. The pH was adjusted 3.8 to 4.0 using sulphuric acid at 5-10° C. and stirred for an hour. The product was filtered and washed with water. The product was then dried to result in amorphous diprotected meropenem of compound formula (V) (FIG. 1).

The isolated wet product was dissolved in THF (550 mL), then water (400-450 mL) added and the pH adjusted to 3.8 to 4.5 using sulphuric acid solution. The reaction mass was subjected to hydrogenation with 10% palladium on carbon (55 g) at 25-30° C. with 9-10 kg pressure of hydrogen. The palladium-carbon was filtered off and the filtrate washed with ethyl acetate. The aqueous layer was charcoalised. To the aqueous filtrate was added slowly cold acetone. The product was filtered and washed with aqueous acetone to afford the title compound (23.5 g) as off-white crystal.

(c). Preparation of Meropenem Trihydrate

To a solution of (4R,5R,6S)-3-[(diphenoxyphosphoryloxy]-6-[(R)-1-hydroxyethyl]-4-methyl-7-oxo-1-azabicyclo[3.2.0]hept-2-ene-2-carboxylic acid (4-nitrophenyl)methyl ester (50 g) and (2S,4S)-1-p-nitrobenzyloxycarbonyl-2-dimethylaminocarbonylamino-4-mercaptopyrrolidine (33 g) in N,N-dimethylformamide (250 mL) was added slowly diisopropylethylamine (14 g) at −40 to −10° C. and stirred for 2-3 h. The reaction mass was added slowly to the water at 3 to 10° C. to isolate the solid product. The pH was then adjusted to 3.8 to 4.0 using sulphuric acid at 5 to 10° C. and stirred for an hour. The product was filtered and washed with water.

The isolated wet product was dissolved in THF (550 mL), then water (400-450 mL) added. The reaction mass was subjected to hydrogenation with 10% palladium on carbon (55 g) at 25-30° C. with 9-10 kg pressure of hydrogen. The palladium-carbon was filtered off and the filtrate washed with ethyl acetate. The aqueous layer was charcoalised. To the aqueous filtrate was added slowly cold THF. The product was filtered and washed with aqueous THF to afford the title compound (22.0 g) as off white crystal.

Advantages:

The known process described in literature for the isolation of compound of formula (V) involves the usage of ethyl acetate or ethyl acetate/heptane or hexane or IPE. The present invention obviates the use of multiple solvent, and hence economically advantageous over the existing process. Also the present process obviates the risk involved in the recovery of solvent by distillation. The present invention provides a simple isolation technique for the compound of formula (V).

We claim:

1. A process for the preparation of purified Meropenem trihydrate of the formula (I), which comprises the steps of:

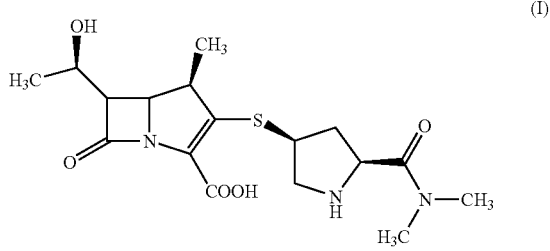

(a) dissolving the Meropenem or its hydrate salt in water in the presence of base and in the presence or absence of water-miscible organic solvents,
(b) optionally filtering through micron filter,
(c) adjusting the pH to 4.0 to 7.0, and
(d) adding solvent to yield the Meropenem trihydrate of formula (I).

2. The process as claimed in claim 1, wherein the base used in step (a) is selected from ammonia, sodium hydroxide, sodium carbonate, potassium carbonate, sodium bicarbonate, potassium bicarbonate, diethylamine, diisopropylamine, triethylamine, diisopropylethylamine, sodium acetate, sodium lactate, sodium-2-ethyl hexanoate and water-miscible organic solvents used in step (a) is selected from acetone, acetonitrile, methanol, ethanol, isopropanol, 1-propanol, THF or mixtures thereof.

3. The process as claimed in claim 1, wherein the pH in step (c) is adjusted using an acid selected from formic acid, HC1, sulfuric acid, phosphoric acid, or acetic acid.

4. The process as claimed in claim 1, wherein the solvent used in step (d) is selected from THF, acetone, methyl ethyl ketone, methanol, iso-propanol, 1-propanol, ethanol or mixtures thereof.

* * * * *